United States Patent [19]
Hayama et al.

[11] Patent Number: 5,362,485
[45] Date of Patent: Nov. 8, 1994

[54] HAIR COSMETIC COMPOSITIONS COMPRISING SULFIDE LINKED POLYSILOXANES

[75] Inventors: Kazuhide Hayama; Kanji Narazaki; Yukio Saitoh; Tomoaki Hiwatashi; Isao Itoh; Sigeoki Kawaguchi, all of Yokkaichi, Japan

[73] Assignee: Mitsubishi Petrochemical Company, Ltd., Tokyo, Japan

[21] Appl. No.: 96,257

[22] Filed: Jul. 26, 1993

[30] Foreign Application Priority Data

Jul. 28, 1992 [JP] Japan .................... 4-201373

[51] Int. Cl.$^5$ .................... A61K 7/06; A61K 7/08; A61K 7/09
[52] U.S. Cl. .................... 424/70; 424/71
[58] Field of Search .................... 424/70, 71

[56] References Cited

U.S. PATENT DOCUMENTS 5,100,658 3/1992 Bolich, Jr. et al. .................... 424/71

Primary Examiner—Thurman K. Page
Assistant Examiner—Peter F. Kulkosky
Attorney, Agent, or Firm—Oblon, Spivak, McClelland, Maier & Neustadt

[57] ABSTRACT

A hair cosmetic composition containing a graft copolymer or an alternating block copolymer, each of which comprises a first unit containing a polysiloxane group and a second unit containing a polymer of unsaturated monomers is provided. The first and second units are linked by sulfide linkage. The hair cosmetic composition provides hair with softness, luster, combing smoothness, styling ease, enhanced volume, and has good hairstyle retainability and damage-restoring characteristics.

15 Claims, No Drawings

HAIR COSMETIC COMPOSITIONS COMPRISING SULFIDE LINKED POLYSILOXANES

BACKGROUND OF THE INVENTION

1. Field of the Invention

The present invention relates to a hair cosmetic composition suitable for setting or conditioning hair. Further, the present invention relates to a novel polymer suitable for preparing a hair cosmetic composition and, more particularly, to a polymer having polysiloxane groups so as to provide hair with good luster and gloss and smooth texture. The hair cosmetic composition of the present invention is suitable for maintaining a hairstyle (setting hair) and for conditioning hair, more specifically, for providing hair with softness, luster, combing smoothness, styling ease and enhanced volume, as well as for restoring damaged hair.

2. Description of the Related Art

Known organic solvent-based hair cosmetics containing water and/or alcohols, for example, shampoos, conditioners, rinses, treatment lotions, setting preparations, permanent wave lotions and mascara, contain emulsified, solubilized or dissolved oil ingredients, such as silicone-based compounds, fatty acid ester-based compounds or hydrocarbon-based compounds, for providing hair with luster, gloss and smoothness. Silicone-based compounds in particular are widely used these days because of their good characteristics.

Such silicone-based compounds are used in, for example: hair cosmetics containing silicone oils, such as ① polydimethylsiloxane or polymetylphenylsiloxane, and/or emulsions thereof; ② hair cosmetics containing hair-styling resins, such as cationic polymers and/or amphoteric polymers containing ether-modified silicone, such as polydimethylsiloxane-polyoxyalkylene block copolymers (as disclosed in Japanese Patent Laid Open Nos. 63-135319, 63-180814, 63-183520 and 1-128915); ③ shampoos, and rinses composed of amino-modified organopolysiloxane emulsions (as disclosed in Japanese Patent Laid Open No. 63-307811); ④ treatment preparations containing cationic polymers and amino-modified organopolysiloxane emulsions and hair-styling preparations containing amphoteric polymers and the said emulsions (as disclosed in Japanese Patent Laid Open No. 63-275515); and ⑤ hair cosmetics containing high-molecular polydimethylsiloxane, polymethylphenylsiloxane, or the like (as disclosed in Japanese Patent Laid Open No. 63-243019).

However, the known hair cosmetics containing silicone-based compounds have problems, such as if large amounts of silicone oils and/or ether-modified silicones are included in the hair cosmetics or they are used for a long period of time, they are liable to render the hair sticky or to be transferred from the hair to the hands or clothing, the emulsion type hair cosmetics do not have good dispersion stability; and high-molecular silicones cannot be applied to a wide range of hair cosmetics because they have rather poor compatibility with hair-styling resins, various additives or the like, and thus limiting their free formulations.

Further, because silicone-based compounds not having hydrophilic groups, such as polyether groups, are not easily removed from hair by ordinary washing, they turn the hair hydrophobic if a hair cosmetic containing silicone-based compounds is applied to the hair repeatedly for a long period of time, thereby causing problems in dying or permanent-wave treatment, or the like.

To eliminate the above problems, Japanese Patent Laid Open Nos. 2-25411, 3-128909 and 3-128311 disclose hair cosmetics employing polysiloxane-based graft polymers obtained by copolymerizing polysiloxane group-containing unsaturated monomers and hydrophilic unsaturated monomers and/or hydrophobic unsaturated monomers. However, production of these polysiloxane-based graft polymers entail some problems, as polysiloxane group-containing unsaturated monomers do not easily copolymerize with the counter parts. Further, to fully achieve the effects of the polysiloxane groups, the copolymerization ratio of the polysiloxane group-containing unsaturated monomers must be increased.

An object of the present invention is to provide a hair cosmetic containing a novel polymer which eliminates the above-stated problems such as limited free formulations and, more specifically, provides hair with luster, gloss and smooth texture without making the hair sticky, and does not accumulate on the hair even if it is repeatedly used for a long period of time, and which facilitates incorporating polysiloxane groups into a polymer regardless of the molecular weights of the polysiloxane groups so as to easily and fully achieve the effects of the polysiloxane.

SUMMARY OF THE INVENTION

In order to achieve the above objects, according to the present invention, there is provided a hair cosmetic composition comprising a graft copolymer and/or an alternating block copolymer, each of which comprises a first unit containing a polysiloxane group and a second unit containing a polymer of unsaturated monomers, said two types of units being bonded through sulfide linkage.

The hair cosmetic composition of the present invention containing a graft copolymer and/or an alternating block copolymer can eliminate the problems caused by the conventional silicone-based compounds, such as if a large amount of silicone-based compounds are included in a hair cosmetic or it is used for a long period of time, it is liable to make the hair sticky or to be transferred to clothing or other parts of the body, such as the hands. Further, by selecting a suitable unsaturated monomer for producing such a polymer, the hair cosmetic composition of the present invention can be easily removed from the hair by ordinary washing and a restriction for free formulations can be eliminated.

Further, according to the present invention, introduction of the polysiloxane group-containing unit into the graft or alternating block copolymer can be achieved by a mercapto group-containing polysiloxane. And owing to the reaction characteristics of the mercapto groups, the units containing polysiloxane groups can be bonded with the units containing polymer of unsaturated monomer through sulfide linkages regardless of the molecular weights of the polysiloxane group.

The hair cosmetic composition of the present invention produced in a manner described above shows excellent performance in setting and conditioning hair providing hair with softness, good luster and gloss, combing smoothness, styling ease and enhanced volume, good hairstyle retainability as well as for restoring damaged hair.

DETAILED DESCRIPTION OF THE INVENTION

The present invention will be described in detail hereinafter.

I. Graft Copolymer or Alternating Block Copolymer Linked by Sulfide Linkage

It is widely known that when unsaturated monomers are radical-polymerized in the presence of a mercapto group-containing compound, the mercapto group-containing compound serves as a radical capturing agent, thereby, a polymer of unsaturated monomers is bonded to the residue of the mercapto group-containing compound through sulfide linkage, thus forming a polymer.

A polymer contained in the hair cosmetic composition of the present invention can be produced by using this technique. More specifically, unsaturated monomers are radical-polymerized in the presence of one or more polysiloxane compounds in which each molecule contains at least one mercapto group, for example, polysiloxane compounds as represented by the general formulae (3) and (4) in which one molecule has n or (2+p) o-f mercapto groups.

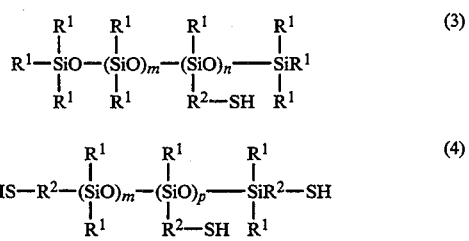

where $R^1$ represents a hydrogen atom, an alkyl group of C1 to C10, a phenyl group, a hydroxy terminated polyoxyalkylene group, a polyoxyalkylene group substituted with an alkyl ether or a fatty acid ester, a polyalkylenepolyamine group, a fatty acid group, or a polysiloxane group; $R^2$ represents an alkylene group of C1 to C10; and m, n and p represent the numbers of groups contained in each polysiloxane group, m being an integer within a range of from 10 through 350, n being an integer within a range from 1 through 50, and p being an integer within a range of from 0 through 50.

An unsaturated monomer is radical-polymerized in the presence of a mercapto group-containing compound represented by general formula (3) to obtain a graft copolymer in which a unit composed of a polymer of the unsaturated monomer is sulfide-linked to a unit containing a polysiloxane group represented by general formula (1).

Further, an unsaturated monomer is radical-polymerized in the presence of a mercapto group-containing compound represented by general formula (4) to obtain a graft copolymer or an alternating block copolymer in which a unit composed of a polymer of the unsaturated monomer is sulfide-linked to a unit containing a polysiloxane group represented by general formula (2).

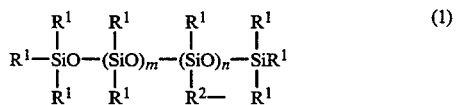

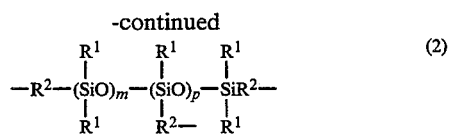

where the symbols $R^1$, $R^2$ m n and p mean the same as defined above.

In a graft copolymer or an alternating block copolymer contained in the hair cosmetic composition of the present invention, all of the mercapto groups of a polysiloxane compound may not necessarily form linkages to the polymers composed of unsaturated monomers as long as at least one of the mercapto residues thereof links to the polymer of an unsaturated monomer unit through sulfide linkage.

Units composed of a polymer of an unsaturated monomer can be sulfide-linked to a unit containing a polysiloxane group up to a number equal to the number of mercapto groups of a molecule of the polysiloxane compound used, more specifically, up to a number n if a compound represented by general formula (3) is used, or a number (2+p) if a compound represented by general formula (4) is used. Further, if a peroxide, such as a benzoyl peroxide, is used for the radical polymerization as described later, a block copolymer having increased numbers of sulfide linkages can be produced as radicals generated by hydrogen-extracting reaction further react with mercapto groups of other polysiloxane.

A copolymer contained in the hair cosmetic composition of the present invention preferably has a molecular weight within a range between 10,000 and 1,000,000.

I.1 Mercapto Group-containing Polysiloxane Compound

The mercapto group-containing polysiloxane compounds used for producing a polymer having sulfide linkages according to the present invention are polysiloxane compounds, as represented by the general formula (3) or (4) having at least one mercapto group. Any single compound or a combination of two or more compounds selected from the compounds of the general formulae (3) and the compounds represented by general formula (4) may be used.

Some compounds represented by general formula (3) are commercially available as, for example, BX16-838A (Toray Dow Corning Silicone: m=250, n=5, $R^1$=methyl group, $R^2$=propylene group in general formula (3): referred to as mercaptopolysiloxane BX16 in Examples); X-22-980 (Shin-Etsu Chemical: m=150, n=4, $R^1$=methyl group, $R^2$=propylene group in general formula (3): referred to as mercaptopolysiloxane X22 in Examples); and KP-358 (Shin-Etsu Chemical; m=50, n=4, $R^1$=methyl group, $R^2$=propylene group in general formula (3): referred to as mercaptopolysiloxane KP358 in Examples). An example of commercially available compounds represented by general formula (4) is X-22-167B (Shin-Etsu Chemical: m=40, p=0, $R^1$=methyl group, $R^2$=propylene group in general formula (4): referred to as mercaptopolysiloxane X-B in Examples).

A suitable weight ratio of the first unit containing a polysiloxane group to the second unit composed of a polymer of an unsaturated monomer contained in a produced graft copolymer or alternating block copolymer is within a range of 0.5-85/99.5-15 and, more preferably, 1-75/99-25.

If the amount of the first unit containing a polysiloxane is less than 0.5% by weight, the resulting polymer fails to provide hair with good luster, gloss and smooth texture. If it is greater than 85% by weight, the resulting polymer causes problems when it is formulated for making a hair cosmetic or applied to hair repeatedly for a long period of time.

I.2 Unsaturated Monomer

The unsaturated monomer forming part of a graft copolymer or an alternating block copolymer according to the present invention can be any monomer selected from hydrophilic unsaturated monomers (a) and/or hydrophobic unsaturated monomers (b) as follows. Any combination of monomers selected from either of the monomer groups (a) and (b) can also be used.

(a) The hydrophilic unsaturated monomers are cationic, anionic, nonionic or amphoteric unsaturated monomers having radical polymerization characteristics, and generally have water-solubility of 10 (g/100 g of water, at 25 C.) or greater.

Examples of the cationic unsaturated monomers are: monomers derived from acrylic acid or methacrylic acid (hereinafter, collectively referred to as (meth) acrylic acid) and an epihalohydrin-quarternized compound of trialkylamine of C1 to C4, such as (meth) acrylic hydroxypropyltrimethylammonium chloride, and (meth) acrylic hydroxypropyltriethylammonium bromide; amine-derivatives of (meth) acrylic acid or (meth) acrylamide derived from (meth) acrylic acid or (meth) acrylamide and dialkylalkanolamine having C1 to C4 alkyl groups, such as dimethylaminoethyl (meth) acrylate, diethylaminoethyl (meth) acrylate and dimethylaminopropyl (meth)acrylate; and dimethylaminopropyl (meth) acrylamide.

Examples of the cationic unsaturated monomers further include: neutralized products of the amine-derivatives of (meth) acrylic acid and (meth) acrylamide with hydrochloric acid, lactic acid or the like; modified products thereof with alkyl halide such as methyl chloride, ethyl chloride, methyl bromide or ethyl iodide; modified products thereof with halogenated fatty acid ester such as ethyl monochloroacetate and methyl monochloropropionate; and modified products thereof with dialkyl sulfate such as dimethyl sulfate and diethyl sulfate.

Further included are amine-derivatives of allyl compounds such as diallyl dimethylammonium chloride.

The cationic unsaturated monomers can be used in the form of monomers for copolymerization. Alternatively, they may be used in the form of precursors for copolymerization and then modified into cations with a modifying agent. For example, dimethylaminoethyl (meth)acrylate, a precursor, is copolymerized and then modified into cations with a modifying agent such as a hydrochloric acid, ethyl monochloroacetate or dimethyl sulfate.

Examples of the anionic unsaturated monomers are: unsaturated carboxylic acid monomers, such as (meth) acrylic acid, maleic acid, maleic anhydride, itaconic acid, fumaric acid and crotonic acid; half esters of unsaturated polybasic acid anhydride (e.g., succinic anhydride and phthalic anhydride) and hydroxyl group-containing (meth)acrylate (e.g., hydroxyethyl (meth) acrylate and hydroxypropyl (meth)acrylate); monomers having sulfonic acid groups, such as styrene sulfonic acid and sulfoethyl (meth)acrylate; monomers having phosphoric acid groups, such as acid phosphoxyethyl (meth)acrylate, and 3-chloro-2-acid phosphoxypropyl (meth)acrylate.

These anionic monomers can be used in the form of acid or partially or completely neutralized forms for copolymerization. Alternatively, they can be used in the form of acid, followed by partial or complete neutralization after copolymerization. Examples of the bases used for neutralization are: alkali metal hydroxides, such as lithium hydroxide, potassium hydroxide and sodium hydroxide; amine compounds, such as ammonium aqueous solution, mono-, di- or triethanolamine, triethylamine, morpholine, aminomethyl propanol, and aminoethyl propanediol.

Examples of the nonionic unsaturated monomers are monomers derived from alkyleneoxides of C2-C4 and (meth)acrylic acid, such as, hydroxyethyl (meth) acrylate, ployethyleneglycol-mono (meth) acrylate, methoxypolyethyleneglycol mono(meth)acrylate, methoxypoly(ethyleneglycol/propyleneglycol) mono(meth)acrylate and polyethyleneglycol di(meth)acrylate, and (meth)acrylamide.

Example of amphoteric unsaturated monomers are: neutralized products of amine-derivatives of (meth)acrylic acid or (meth) acrylamide with monochloroacetic acid/aminomethyl propanol; monochloroacetic acid/triethanolamine neutralized products; modified products with halogenated fatty acid salts such as potassium monochloroacetate and sodium monochloropropionate; and modified products with propanesultone.

Like the cationic unsaturated monomers aforementioned, the amphoteric unsaturated monomers can be used in the form of monomers for copolymerization, and also can be used in the form of precursors for copolymerization followed by modifying to amphoteric compounds by using a modifying agent. Salts produced as byproducts by the ampho-ionic modification can be removed by filtration, ion exchange, etc., either before or after copolymerization and ampho-ionic modification. Such techniques are described in detail in Japanese Patent Laid Open No. 56-92809.

(b) The hydrophobic unsaturated monomers are used for providing the resulting polymers with hydrophobicity, and film strength, hardness and softness. They have radical polymerization ability and water-solubility of 10 (g/100 g of water, at 25° C. ) or less.

Example of the hydrophobic monomers are: saturated and unsaturated alkyl (meth)acrylates of C1 to C24, such as methyl (meth)acrylate, allyl (meth)acrylate, isobutyl (meth)acrylate, cyclohexyl (meth)acrylate, octyl (meth)acrylate, lauryl (meth)acrylate, oleyl (meth)acrylate, and behenyl (meth)acrylate; hydrophobic (meth)acrylate-based derivatives, such as butoxyethyl (meth)acrylate, benzyl (meth)acrylate, tetrahydrofurfuryl (meth)acrylate, ethyleneglycol di(meth)acrylate, and 1,3-butyleneglycol di(meth)acrylate, diacetone acrylamide; aromatic unsaturated monomers, such as styrene, chlorostyrene, and vinyl toluene; and vinyl acetate.

A suitable amount of the unsaturated monomer used is such that a weight ratio of the first unit containing a polysiloxane group to the second unit composed of a polymer of the unsaturated monomer in the resulting graft copolymer or alternating block copolymer is within a range of 0.5–85/99.5–15 and, more preferably, 1–75/99–25.

The amount of a hydrophilic unsaturated monomer (a) used can be suitably selected. A preferable amount thereof used for preparing a hair cosmetic suitable for conditioning hair, such as a shampoo, a rinse, a treatment lotion or permanent wave lotion, is 100–25% by weight of the total weight of the unsaturated monomers used. A preferable amount thereof used for preparing a hair cosmetic suitable for setting hair, such as a set lotion or a mascara, is 80–0% by weight of the total weight of the unsaturated monomers used.

The amount of a hydrophobic unsaturated monomer (b) used can also be suitably selected. A preferable amount thereof used for preparing a hair cosmetic suitable for conditioning hair is 0–75% by weight of the total weight of the unsaturated monomers used, while in a cosmetic suitable for setting hair 20–100% by weight is preferable.

I.3 Polymerization

A graft copolymer or an alternating block copolymer having sulfide linkages according to the present invention can be produced by copolymerization of an unsaturated monomer in the presence of a mercapto group-containing polysiloxane compound by a known radical polymerization method, such as bulk polymerization, solution polymerization, suspension polymerization or emulsion polymerization.

A preferred method is solution polymerization in which a mercapto group-containing polysiloxane compound and one or more kinds of unsaturated monomer are dissolved in a solvent, and then copolymerization is carried out by adding a polymerization initiating agent in a nitrogen atmosphere while the solution is heated and stirred.

Examples of the solvent are: water; alcohol, such as methanol, ethanol, isopropanol, ethyleneglycol and butyl cellosolve; acetone; toluene; and ethyl acetate. These solvents may be used in combination. Preferred polymerization initiators are: peroxides, such as benzoyl peroxide or lauroyl peroxide; and azo compounds, such as azobisisobutyronitrile.

Although all the ingredients for copolymerization, that is, a mercapto group-containing polysiloxane compound and unsaturated monomers, are added to a solvent before initiation of the reaction in the normal procedure, they may be added separately and stepwise, in terms of kind and/or amount during the reaction. A preferred amount of the solvent is such that the polymer concentration in the resulting copolymer solution becomes 10–65% by weight.

Although the mercapto group-containing polysiloxane compound, one of the essential ingredients according to the present invention, serves as a chain transfer agent, the molecular weight of the resulting polymer can be desirably varied by changing polymerization conditions, such as, polymerization temperature, the kind and amount of polymerization initiator, the amount of solvent, and other conditions such as other chain transfer agents, etc. The preferred molecular weight of the resulting copolymer is within a range of 10,000–1,000,000.

The polymer formed can be obtained as a solid by removing the solvent from the resultant solution. The polymer can be used as a desired solution by diluting it with a suitable solvent. Further, a combination of two or more kinds of polymers thus formed or solutions thereof can be suitably used.

II. Use of the Copolymer

A copolymer obtained as described above is added to known compositions for hair cosmetics, such as shampoos, rinses, treatment preparations, setting preparations, permanent wave lotions or mascara, to a concentration by weight of preferably 0.1% or greater, and more preferably, 0.1–10% by weight. The hair cosmetic composition may be in any form, for example, liquid, cream, emulsion or gel. The copolymer of the present invention may used together with known natural polymers, modified natural polymer or synthetic polymers.

Typical preparations are as follows:

1) For preparing a shampoo, the copolymer is added to a base composition containing a known anionic, amphoteric or nonionic surfactant. Further, various known additives may be added, such as a foam enhancing agent, a viscosity enhancing agent, hydrotrope, an opacifying agent, a conditioning agent, a sterilizing agent, or a flavor.

2) For preparation of a rinse or a treatment, the copolymer is added to a base composition containing a known cationic surfactant. Further, various known additives may be added, for example, oils and fats, cationic and amphoteric polymers, a moisture keeping agent, a solubilizing agent, an emulsifying agent, a viscosity enhancing agent, an opacifying agent, a sterilizing agent, a hair nourishing agent, or a flavor.

3) For preparation of a mascara and setting preparations, the setting preparations including various hair styling cosmetics, such as aerosol type hair spray, pump type hair spray, foam type aerosol, hair mist, setting lotion, hairstyling gel, hair liquid, hair cream, hair oil, etc., the copolymer of the present invention is used in place of the known setting polymers and polysiloxane-based polymer. Further, a known setting polymer and various known additives, such as oils and fats, a moisture keeping agent, a solubilizing agent, an emulsifying agent, a viscosity enhancing agent, an opacifying agent, a sterilizing agent, a flavor, etc., may be added.

4) For preparation of a permanent wave lotion, the copolymer is added to a known base composition containing oxidation reduction agents, such as bromic acid salts, perboric acid salts, thioglycolic acid and salts thereof, cystine, etc. Further, various known additives may be added, for example, a surfactant, a thickening agent, a stabilizing agent, an opacifying agent, conditioning agent, a wetting agent, a sterilizing agent or a flavor.

EXAMPLES

The present invention will be further described with reference to Polymer Production Examples and Examples, but the invention is not intended to be limited thereto. In the Polymer Production Examples, "part" and "%" are determined based on weight. In the Examples, "part" and "%" are determined based on weight regarding effective components.

Polymer Production Example 1

5 parts of mercapto polysiloxane BX16, 90 parts of diethylaminoethyl methacrylate, 5 parts of stearyl methacrylate and 55 parts of anhydrous ethanol were placed in a five-necked flask equipped with a reflux condenser, a dropping funnel, a thermometer, a glass inlet tube for nitrogen substitution and a stirrer. While heating at reflux temperature of 80° C. in a nitrogen atmosphere, a solution prepared by dissolving 0.6 part of azobisisobutyronitrile in 33 parts of ethanol was dropped through the dropping funnel into the five-necked flask over 3 hours. Subsequently, 0.3 part of azobisisobutyronitrile was added to continue polymerization for another 6 hours.

After cooling the reaction solution the same amount by mole of diethyl sulfate as the mole of the diethylaminoethyl methacrylate was dropped through the dropping funnel into the five-necked flask to conduct cationization reaction in an atmosphere of nitrogen at 50° C. for 2 hours. Then, the solvent was removed, and the recovered solid was dissolved in pure water to obtain an aqueous solution of a polymer.

The resultant polymer is referred to as P-1. The average molecular weight of the polymer was 300,000.

Production Example 2

10 parts of mercapto polysiloxane BX16, 90 parts of dimethylaminoethyl methacrylate, 5 parts of stearyl methacrylate and 100 parts of anhydrous ethanol were placed in generally the same five-necked flask as used in Polymer Production Example 1. After addition of 1 part of azobisisobutyronitrile, the resultant solution was refluxed at 80° C. in a nirogen atmosphere for 7 hours to conduct copolymerization. Then, an anhydrous ethanol solution containing 50% aminomethyl propanol-neutralized monochloroacetic acid, whose amount by mole was the same as the mole of the dimethylaminoethyl methacrylate, was added through the dropping funnel into the five-necked flask. The resultant solution was refluxed at 80° C. in a nitrogen atmosphere for 6 hours to conduct ampho-ionization reaction. Then, the ethanol was removed by evaporation while pure water was being added through the dropping funnel into the five-necked flask, thus obtaining a polymer aqueous solution.

The thus-obtained polymer is referred to as P-2. The average molecular weight of the polymer was 70,000.

Polymer Production Example 3

70 parts of mercapto polysiloxane KP358, 30 parts of dimethylaminopropyl methacrylamide and 100 parts of anhydrous ethanol were placed in generally the same five-necked flask as used in Polymer Production Example 1. After addition of 0.6 part of azobisisobutyronitrile the resultant solution was refluxed at 80° C. in a nitrogen atmosphere for 8 hours to conduct copolymerization. Then, butyl chloride whose amount by mole was the same as the mole of the dimethylaminopropyl methacrylate was added through the dropping funnel into the five-necked flask. The resultant solution was refluxed at 80° C. in a nitrogen atmosphere for 6 hours to conduct cationization reaction.

The thus-obtained polymer is referred to as P-3. The average molecular weight of the polymer was 5,000.

Polymer Production Example 4

15 parts of mercapto polysiloxane BX16, 40 parts of dimethylaminoethyl methacrylate, 10 parts of methyl methacrylate, 10 parts of isobutyl acrylate, 25 parts of stearyl methacrylate and 67 parts of anhydrous ethanol were placed in generally the same five-necked flask as used in Polymer Production Example 1. The mixture was refluxed at 80° C. in a nitrogen atmosphere and a solution prepared by dissolving 0.6 part of azobisisobutyronitrile in 33 parts of ethanol was dropped through a dropping funnel into the five-necked flask over 3 hours, followed by addition of 0.3 part of azobisisobutyronitrile to carry out copolymerization for further 6 hours.

Then, anhydrous ethanol suspension containing the same amount by mole of potassium hydroxide-neutralized monochloroacetic acid as the mole of the dimethylaminoethyl methacrylate was added through the dropping funnel into the five-necked flask. The resultant solution was refluxed at 80° C. in a nitrogen atmosphere for further 12 hours to conduct amphoionization reaction.

The resultant viscous suspension was subjected to filtration by using a pressure filter. The filtrate was loaded on a column filled with restored cation exchange resin (DIAION PK-220: a system was substituted with anhydrous ethanol after restoration) followed by anion exchange by using a column filled with restored anion exchange resin (DIAION PA-416: a system was substituted with anhydrous ethanol after restoration).

The resultant polymer is referred to as P-4. The average molecular weight of the polymer was 150,000.

Polymer Production Example 5

20 parts of mercapto polysiloxane BX16, 10 parts of acrylic acid, 15 parts of methacrylic acid, 10 parts of styrene, 10 parts of methyl methacrylate, 10 parts of tert-butyl acrylate 25 parts of stearyl methacrylate and 100 parts of acetone were placed in generally the same five-necked flask as used in Polymer Production Example 1. After addition of 0.3 part of benzoyl peroxide the resultant solution was refluxed at 60° C. in a nitrogen atmosphere for 10 hours to conduct copolymerization.

Then, the solution was heated to evaporate the acetone while ethanol was being added through a dropping funnel into the five-necked flask, thus obtaining an ethanol solution of a polymer.

After the reaction solution was cooled, an ethanol (containing 5% water) solution containing 50% aminomethylpropanol, whose amount by mole was 80% of the total mole of the acrylic acid and the methacrylic acid, was dropped through the dropping funnel into the five-necked flask.

The thus-obtained polymer is referred to as P-5. The average molecular weight of the polymer was 500,000.

Polymer Production Example 6

3 parts of mercapto polysiloxane X-B, 40 parts of dimethylaminoethyl methacrylate, 40 parts of N-vinyl pyrrolidone, 17 parts of methyl methacrylate and 12 parts of anhydrous ethanol were placed in generally the same five-necked flask as used in Polymer Production Example 1. After addition of 0.6 part of azobisisobutyronitrile the resultant solution was refluxed at 80° C. in a nitrogen atmosphere for 8 hours to conduct copolymerization.

Then, the same amount by mole of propane sultone as the mole of the dimethylaminoethyl methacrylate was added through a dropping funnel into the five-necked flask to conduct amphoionization reaction at 80° C. in a nitrogen atmosphere for 6 hours.

The thus-obtained polymer is referred to as P-6. The average molecular weight of the polymer was 70,000.

Polymer Production Example 7

20 parts of mercapto polysiloxane BX16, 20 parts of 2-ethylhexyl methacrylate, 60 parts of lauryl methacrylate and 100 parts of isopropyl alcohol were placed in generally the same five-necked flask as used in Polymer Production Example 1. After addition of 0.6 part of azobisisobutyronitrile the resultant solution was refluxed at 80° C. in a nitrogen atmosphere for 8 hours to conduct copolymerization.

The thus-obtained polymer is referred to as P-7. The average molecular weight of the polymer was 600,000.

Polymer Production Example 8

35 parts of mercapto polysiloxane X22, 40 parts of N-vinyl pyrrolidone, 10 parts of hydroxyethyl methacrylate, 15 parts of tridecyl methacrylate and 100 parts of anhydrous ethanol were placed in generally the same five-necked flask as used in Polymer Production Example 1. After addition of 0.6 part of azobisisobutyronitrile the resultant solution was refluxed at 80° C. in a nitrogen for 8 hours to conduct copolymerization.

The thus-obtained polymer is referred to as P-8. The average molecular weight of the polymer was 30,000.

Example 1

The following shampoo composition was prepared:

|  | % |
|---|---|
| AEROSOL A-102 (note 1) | 20 |
| Lauroyldiethanolamide | 2 |
| P-1 | 2 |
| Flavor | 0.2 |
| Antiseptic | 0.1 |
| Coloring | a very small amount |
| Pure Water | balance |
|  | 100% | note 1: AEROSOL A-102 is disodium sulphosuccinic acid monoester sold by Mitsui Cyanamid.

This shampoo composition was used to wash hair. As a result, the hair was easy to comb just after being washed. After being dried, the hair had good luster, gloss and smooth texture, and was easy to comb.

Repeated use of the shampoo caused no adverse effects such as sticky hair.

Example 2

The following shampoo composition was prepared:

|  | % |
|---|---|
| Sodium Polyoxyethylenelaurylsulfate (3EO) | 10 |
| Sodium Lauroylsulfate | 8 |
| Lauroyldiethanolamide | 2 |
| P-2 | 1 |
| Pure Water | balance |
|  | 100% |

This shampoo composition was used to wash hair. The result was excellent and generally the same as in Example 1.

Example 3

The following shampoo composition was prepared:

|  | % |
|---|---|
| Coconut Oil Fatty Acid Dimethylaminosulfobetaine | 10 |
| Sodium Polyoxyethylenelaurylsulfate (3EO) | 5 |
| P-2 | 0.5 |
| Pure Water | balance |
|  | 100% |

This shampoo composition was used to wash hair. The result was excellent and generally the same as in Example 1.

Example 4

The following rinse composition was prepared:

|  | % |
|---|---|
| Stearyltrimethylammonium Chloride | 1.5 |
| Cetanol | 2 |
| P-1 | 0.2 |
| Pure Water | balance |
|  | 100% |

This rinse composition was used to rinse hair. As a result, the hair was easy to comb just after being rinsed. After being dried, the hair had good luster, gloss and smooth texture, and was easy to comb.

Repeated use of the rinse caused no adverse effects such as sticky hair.

Example 5

The following rinse composition was prepared:

|  | % |
|---|---|
| Distearyltrimethylammonium Chloride | 1.5 |
| P-3 | 1 |
| Flavor | 0.1 |
| Pure Water | balance |
|  | 100% |

This rinse composition was used to rinse hair. The result was excellent and generally the same as in Example 4.

Example 6

The following liquid was placed in a spray can, which was then filled with liquefied petroleum gas (LPG), thus obtaining an aerosol type hair spray composition.

| Liquid containing | 65 parts |
|---|---|
| P-4 | 3 parts |
| Anhydrous Ethanol | 62 parts |
| LPG (3 k/cm$^2$ -G, 20° C.) | 35 parts |

This composition was sprayed to hair. As a result, the composition provided the hair with good hairstyle retainability, good luster, gloss and smooth texture. Application of this hair spray composition to hair and washing the hair were repeated. As a result, no adverse effects, such as stickiness or uneasiness by accumulation of the composite, were caused.

Example 7

The following liquid was placed in a spray can, which was then filled with liquefied petroleum gas (LPG) and dimethyl ether, thus obtaining a water-bearing aerosol type hair spray composition.

| Liquid containing | 70 parts |
|---|---|
| P-5 | 3 parts |
| Pure Water | 20 parts |
| Anhydrous Ethanol | 47 parts |
| Dimethyl Ether | 15 parts |
| LPG (3 k/cm$^2$ -G, 20° C.) | 15 parts |

This composition was sprayed to hair. The result was excellent and generally the same as in Example 6.

Example 8

By generally the same procedure as in Example 6, a foam type aerosol composition containing the following ingredients was prepared.

| Liquid containing | 88 parts |
|---|---|
| P-4 | 2 parts |
| Yuka former AM-75 R205S (note 2) | 2 parts |
| Polyoxyethylenecetyl Ether (10EO) | 0.3 part |
| Polyoxyethylenecetyl Ether (2EO) | 0.1 part |
| Pure Water | balance |
| LPG (3 k/cm$^2$ -G, 20° C.) | 12 parts | note 2: Yuka former AM-75 R205S is a carboxybetaine-type amphoteric polymer sold by Mitsubishi Petrochemical Co., Ltd.

This composition was sprayed to hair. The result was excellent and generally the same as in Example 6.

Example 9

The following water-containing pump-type hair spray composition was prepared:

| | % |
|---|---|
| P-5 | 3 |
| Pure Water | 45 |
| Anhydrous Ethanol | balance |
| | 100% |

This composition was sprayed to hair. The result was excellent and generally the same as in Example 6.

Example 10

The following hairstyling gel composition was prepared:

| | % |
|---|---|
| Carbopol 940 (note 3) | 1 |
| Aminomethylpropanol | 0.9 |
| P-6 | 3 |
| Anhydrous Ethanol | 15 |
| Pure Water | balance |
| | 100% |

This composition was applied to hair. The result was excellent and generally the same as in Example 6.

Example 11

The following hair oil composition was prepared:

| | % |
|---|---|
| Octamethylcyclotetrasiloxane | 40 |
| P-7 | 8 |
| Anhydrous Ethanol | balance |
| | 100% |

This composition was applied to hair. As a result, the composition provided the hair with good luster and gloss, and smooth texture.

Example 12

The permanent wave lotion composition was prepared:

| | % |
|---|---|
| Thioglycol acid | 6 |
| Monoethanolamine | 7 |
| Emulgen 320P (note 4) | 1 |
| P-8 | 2 |
| Pure Water | balance |
| | 100% | note 4: Emulgen 320P is a polyoxyethylenestearyl ether (13EO) sold by Kao Corp.

This composition was applied to hair, as the first permanent wave lotion, together with the second permanent wave lotion as a conventional method. As a result, the hair was provided with good luster and gloss and smooth texture.

What is claimed is:

1. A hair cosmetic composition comprising 0.1 weight percent or greater of a graft copolymer and/or an alternating block copolymer, each of which comprises;

a first unit containing a polysiloxane group of the general formula (1) and/or (2):

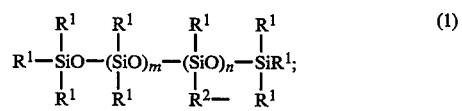

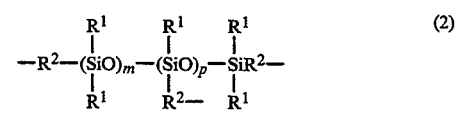

where $R^1$ represents a hydrogen atom, an alkyl group of C1 to C10, a phenyl group, a hydroxy terminated polyoxyalkylene group, a polyoxyalkylene group substituted with an alkyl ether or a fatty acid ester, a polyalkylenepolyamine group, a fatty acid group, or a polysiloxane group; $R^2$ represents an alkylene group of C1 to C10; and m, n and p represent the numbers of groups contained in each polysiloxane group, m being an integer within a range of from 10 through 350, n being an integer within a range from 1 through 50, and p being an integer within a range of from 0 through 50; and a second unit containing a polymer of unsaturated monomers, said first and second units being bonded together at the $R^2$ group of said first unit through a sulfide linkage.

2. The hair cosmetic composition of claim 1 wherein a ratio of the first unit content to the second unit content by weight in said graft copolymer and/or said alternating block copolymer is 0.5-85/99.5-15.

3. The hair cosmetic composition of claim 1 wherein said second unit consists of a polymer of any of the following: acrylic acid, methacrylic acid and derivatives thereof.

4. The hair cosmetic composition of claim 1 wherein said hair cosmetic composition is suitable for setting hair wherein a ratio of a hydrophilic unsaturated monomer content to a hydrophobic unsaturated monomer content by weight in said second unit is 80-0/20-100.

5. The hair cosmetic composition of claim 1 wherein said hair cosmetic composition is suitable for conditioning hair, and wherein a ratio of a hydrophilic unsaturated monomer content to a hydrophobic unsatumonomer content by weight in said second unit is 100-25/0-75.

6. The hair cosmetic composition of claim 1, wherein said composition is a shampoo which further comprises a surfactant selected from the group consisting of an anionic surfactant, an amphoteric surfactant, a nonionic surfactant and a mixture thereof.

7. The hair cosmetic composition of claim 6, further comprising an element selected from the group consisting of a foam enhancing agent, a viscosity enhancing agent, a hydrotrope, an opacifying agent, a conditioning agent, a sterilizing agent, a flavor, and a mixture thereof.

8. The hair cosmetic composition of claim 1, wherein said hair care cosmetic composition is a rinse or treatment, and further comprises a cationic surfactant.

9. The hair cosmetic composition of claim 8, further comprising an element selected from the group consisting of an oil, a fat, a cationic polymer, an amphoteric polymer, a moisture keeping agent, a solubilizing agent, an emulsifying agent, a viscosity enhancing agent, an opacifying agent, a sterilizing agent, a hair nourishing agent, a flavor, and a mixture thereof.

10. The hair cosmetic composition of claim 1, wherein said hair cosmetic composition is a mascara or setting preparation, further comprising an element selected from the group consisting of a setting polymer, an oil, a fat, a moisture keeping agent, a solubilizing agent, an emulsifying agent, a viscosity enhancing agent, an opacifying agent, a sterilizing agent, a flavor, and a mixture thereof.

11. The hair cosmetic composition of claim 1, wherein said hair cosmetic composition is a permanent wave lotion, and further comprises an oxidation reduction agent.

12. The hair cosmetic composition of claim 11, wherein said oxidation reduction agent is selected from the group consisting Of a bromic acid salt, a perboric acid salt, thioglycolic acid, salts of thioglycolic acid, cystine and a mixture thereof.

13. The hair cosmetic composition of claim 11, further comprising an element selected from the group consisting of a surfactant, a thickening agent, a stabilizing agent, an opacifying agent, a conditioning agent, a wetting agent, a sterilizing agent, a flavor and a mixture thereof.

14. The hair cosmetic composition of claim 1, wherein said unsaturated monomers are selected from the group consisting of hydrophilic unsaturated monomers, hydrophobic unsaturated monomers and a mixture thereof.

15. The hair cosmetic composition of claim 1, wherein said hydrophilic monomers are selected from the group consisting of anionic unsaturated monomers, nonionic unsaturated monomers, amphoteric unsaturated monomers and a mixture thereof.

* * * * *